United States Patent [19]
Grigor et al.

[11] Patent Number: 5,833,952
[45] Date of Patent: Nov. 10, 1998

[54] ORAL COMPOSITIONS

[75] Inventors: Janet Grigor, Port Sunlight; Stephen John Raven, Heswall, both of Great Britain

[73] Assignee: Chesebrough-Pond's USA Co., Division of Conopco, Inc., Greenwich, Conn.

[21] Appl. No.: 612,883

[22] PCT Filed: Sep. 9, 1994

[86] PCT No.: PCT/EP94/03027

§ 371 Date: May 10, 1996

§ 102(e) Date: May 10, 1996

[87] PCT Pub. No.: WO95/07682

PCT Pub. Date: Mar. 23, 1995

[30] Foreign Application Priority Data

Sep. 16, 1993 [EP] European Pat. Off. ............. 93307329

[51] Int. Cl.$^6$ ............................ A61K 7/16; A61K 33/30; A61K 31/315; A61K 31/32
[52] U.S. Cl. ............................ 424/49; 424/641; 424/650
[58] Field of Search ......................... 424/49–88

[56] References Cited

U.S. PATENT DOCUMENTS

| | | |
|---|---|---|
| 4,022,880 | 5/1977 | Vinson et al. ............................ 424/49 |
| 4,100,269 | 7/1978 | Pader ....................................... 424/49 |
| 4,138,477 | 2/1979 | Gaffar ...................................... 424/52 |
| 4,469,674 | 9/1984 | Shah et al. .............................. 424/52 |
| 4,689,214 | 8/1987 | Niles et al. .............................. 424/49 |
| 4,814,163 | 3/1989 | Barth ....................................... 424/49 |
| 4,814,164 | 3/1989 | Barth ....................................... 424/49 |
| 4,937,066 | 6/1990 | Vlock ...................................... 424/52 |
| 5,000,944 | 3/1991 | Prencipe et al. ....................... 424/57 |
| 5,094,845 | 3/1992 | Vlock ...................................... 424/52 |
| 5,096,702 | 3/1992 | Rolla et la. ............................. 424/52 |
| 5,188,820 | 2/1993 | Cummins et al. ...................... 424/49 |
| 5,258,173 | 11/1993 | Waterfield .............................. 424/49 |
| 5,405,836 | 4/1995 | Richar et al. ........................... 514/23 |

FOREIGN PATENT DOCUMENTS

| | | |
|---|---|---|
| 0 074 082 | 3/1983 | European Pat. Off. . |
| 0 417 833 | 3/1991 | European Pat. Off. . |
| 0 426 213 | 5/1991 | European Pat. Off. . |
| 0 514 966 | 11/1992 | European Pat. Off. . |
| 2 173 701 | 4/1986 | United Kingdom . |
| 93/07852 | 4/1993 | WIPO . |

*Primary Examiner*—Shep K. Rose
*Attorney, Agent, or Firm*—Milton L. Honig

[57] ABSTRACT

The invention relates to the use of stannous compounds to combat bad breath. Preferably, the stannous compound is used together with a zinc compound. A preferred stannous compound is stannous pyrophosphate, and a preferred zinc compound is zinc citrate. The compounds are preferably included in an oral care composition such as a dentifrice or a mouth wash.

5 Claims, No Drawings

ORAL COMPOSITIONS

This application is filed pursuant to 35 USC S. 371 as a United States National Phase Application of International Application No. PCT/ED 94/03027 filed Sep. 9, 1994 which claims priority EPO 93307329.8 filed Sep. 16, 1993.

BACKGROUND OF THE INVENTION

1. Field of the Invention

The present invention relates to the use of stannous compounds alone or in combination with zinc compounds as effective agents against bad breath and to the use of oral compositions such as dentifrices, mouthwashes, gels, subgingival rinse compositions, toothpastes, toothpowders, chewing gum, prophylactic pastes, lozenges, flosses, toothpicks comprising a stannous compound, either alone or in combination with a zinc compound to combat bad breath (malodour).

2. The Related Art

In the prior art several proposals have been made to combat bad breath (malodour). Many of these proposals have however not resulted in a reasonably effective composition against bad breath (malodour). One of the few really effective oral compositions is based upon the use of a zinc compound. E.g. in U.S. Pat. No. 4,689,214 and EP-A-0,074, 082 oral care products are described which contain a zinc salt and a fluoride, such products having anti-malodour properties. The fluoride can be any of many examples of fluorides, including stannous fluoride. There is, however, no disclosure that the stannous compound as such is the effective agent. It is clear that only zinc was intended to function as effective agent against malodour in combination with fluoride.

Oral compositions which comprise a stannous compound, either alone or in conjunction with a zinc compound, are disclosed in EP-A-0426213, EP-A-0514966, EP-A-0417833 and WO-A-9307852, but these references do not disclose or teach the use of stannous compounds as active agent against bad breath.

SUMMARY OF THE INVENTION

It has now been found that a stannous compound when used alone or in combination with a zinc compound provides an improved anti-bad breath efficacy. Volatile sulphur compounds are considered to be mainly responsible for malodour and bad breath. These may originate from saliva, or from the oral cavity or even the stomach. We have found that stannous compounds are very effective in reducing the level of these volatile sulphur compounds. Not only the effectiveness of the stannous compound alone or particularly in combination with a zinc compound for reducing the level of these volatile sulphur compounds was surprising, but also the long term activity of malodour-inhibition achieved by regular application of an oral composition comprising the active agent(s) according to the present invention was found to be totally unexpected.

DETAILED DESCRIPTION

The stannous compound, suitable for use in the present invention, can be any stannous compound with inorganic or organic counter ions. It can be a highly soluble stannous salt, or it can be a sparingly soluble stannous salt. Highly soluble stannous salts are e.g. stannous fluoride, stannous chloride, stannous chloride fluoride, stannous acetate, sodium stannous fluoride, potassium stannous fluoride, stannous hexafluorozirconate, stannous sulfate, stannous tartrate, stannous gluconate, disodium monostannous citrate, etc. Of these highly soluble stannous salts stannous fluoride is the preferred stannous salt.

Sparingly soluble stannous salts are e.g. stannous pyrophosphate, stannous metaphosphate, stannous oxalate, stannous phosphate, distannous citrate, etc. Stannous pyrophosphate is a preferred sparingly soluble stannous salt. Mixtures of various highly soluble stannous salts may also be used, as well as mixtures of various sparingly soluble stannous salts and mixtures of highly and sparingly soluble stannous salts. A preferred mixture is the mixture of stannous fluoride and stannous pyrophosphate.

Although highly soluble stannous salts can be used in the present invention, they tend to be not sufficiently stable upon storage. The stannous ions, dissolved in an aqueous solution tend to be converted therein to inert tin compounds, which do not provide for an anti-bad breath activity. Therefore, if a highly soluble stannous salt is used, care should be taken to reduce the quantity of active dissolved stannous ions during storage of the oral composition, or to stabilize the stannous ions by other means.

When using a sparingly soluble stannous salt, care should be taken that there is a sufficient level of active dissolved stannous ions in the composition without giving rise to precipitation thereof as e.g. stannous oxide or stannous oxide hydrate. One way of achieving this is by solubilising the stannous salt, e.g. the stannous pyrophosphate with a certain amount of an alkalimetal pyrophosphate, or an alkalimetal citrate, or a fluoride source.

In general, the stannous salt is used in such an amount in the oral composition, that there is an effective amount of active dissolved stannous ions available in the composition to achieve an anti-bad breath effect. For the highly soluble stannous salts this amount will generally range from 0.01–10%, preferably from 0.02–5 and particularly preferably from 0.1–3% by weight of the oral composition. As regards the sparingly soluble stannous salts these ranges are 0.05–10, preferably 0.1–5 and particularly 0.1–3% by weight of the oral composition.

The zinc compound, suitable for use in the present invention can be any highly soluble or sparingly soluble zinc compound having inorganic or organic counter ions. Suitable examples of such zinc salts are enumerated in U.S. Pat. No. 4,022,880 (Vinson et al), which is hereby incorporated by way of reference. A preferred zinc salt is zinc citrate trihydrate. In general, the amount of zinc salt used in the present invention ranges from 0.05–5% (calculated as zinc ion), preferably from 0.1–4% and particularly preferably from 0.1–3% by weight of the oral composition.

The oral composition of the present invention may contain an orally acceptable medium which contains usual additional ingredients in conventional amounts, depending upon the final form of the composition, i.e. a dentifrice, a mouthwash, a gel and the like. Thus, as dentifrice it will usually comprise an abrasive cleaning agent in an amount of from 3–75% by weight. Suitable abrasive cleaning agents are milled or unmilled particulate aluminas; silica xerogels, hydrogels and aerogels and precipitated particulate silicas; calciumpyrophosphate; insoluble sodium metaphosphate; calcium carbonate; dicalcium orthophosphate; particulate hydroxyapatite and so on.

Furthermore, the dentifrice may contain a liquid phase comprising water and a humectant in an amount of 10–99% by weight. Typical humectants are glycerol, sorbitol, polyethyleneglycol, polypropyleneglycol, propyleneglycol, hydrogenated partially hydrolyzed polysaccharides and so on.

Binders or thickening agents such as sodium carboxymethylcellulose, hydroxyethylcellulose, hydroxypropylcellulose, xanthan gums, Irish moss, gum tragacanth, finely-divided silicas and hectorites may also be included in the dentifrice in an amount of 0.5–10% by weight. Another conventional ingredient in a dentifrice is an organic surfactant such as a soap, an anionic, nonionic, cationic, ampholytic and/or a zwitterionic synthetic detergent surfactant in an amount of 0.2–5% by weight.

When the composition is in the form of a mouthwash, it will usually contain an alcohol, a solubilizer, and when in the form of a gel it will usually contain a thickening agent.

Various other optional ingredients may be included in the compositions of the invention, such as flavouring agents, sweetening agents such as sodium saccharinate, whitening agents such as titanium dioxide or zinc oxide, preservatives, vitamins such as vitamin C and E, anti-plaque agents such as copper salts, sanguinarine, allantoin, p-aminobenzoic acid derivates, hexetidine, chlorhexidine, 3-(4-propylheptyl)-4-(2-hydroxyethyl)-morpholine, anti-bacterial agents such as Triclosan (2',4,4'-trichloro2-hydroxy-diphenyl ether), anti-calculus agents such as di- and/or tetra-alkalimetalpyrophosphates, pH adjusting agents, colouring agents, anti-caries agents such as casein, casein digests, sodium trimetaphosphate, sodium fluoride and monosodiumfluorophosphate, anti-staining compounds such as silicone polymers, anti-inflammatory agents such as substituted salicylanilides, plant extracts, desensitizing agents for sensitive teeth such as potassium nitrate and potassium citrate, polymers such as polyvinylmethylether-maleic anhydride copolymers and so on.

When the preferred combination of a stannous salt and a zinc salt is used, the stannous salt and zinc salt may be used in the same phase of the oral composition, or they may each be present in a separate phase, e.g. one of them may be present in the stripe phase of a so-called striped toothpaste and the other one may be present in the main phase of such a striped toothpaste. When a fluoride source is also present in the composition, this may also be present in the phase, separate from the stannous salt containing phase.

The oral compositions of the present invention can be formulated to any desirable pH-value. It is preferred that the compositions have a pH of between 3.5 and 5.5.

The present invention will now be further illustrated by the following Examples.

EXAMPLE I

| | % w/w | |
|---|---|---|
| | Test | Placebo |
| Abrasive Silica | 10.00 | 10.00 |
| Thickening Silica | 8.50 | 8.50 |
| Xanthan gum | 0.75 | 0.75 |
| Polyethylene glycol (MW 1500) | 5.00 | 5.00 |
| Sodium lauryl sulphate | 1.50 | 1.50 |
| Titanium dioxide | 1.00 | 1.00 |
| Flavour | 1.00 | 1.00 |
| Sodium fluoride | 0.25 | 0.25 |
| Stannous pyrophosphate | 1.00 | — |
| Zinc citrate trihydrate | 0.50 | — |
| Sorbitol syrup 70% w/w non-crystal. | 68.00 | 68.00 |
| Water (Deionised) | 2.50 | 4.00 |

These formulations were tested according to the following protocol:

1. Panellists brushed for 7 days with control paste (24 total).
2. Split into two random groups of equal size.
3. One group used placebo paste for 2 1 days with malodour measured prior to start (Baseline) and after day 1, 7, 14 and 21. At the end of this period they used a control for 21 days and then evaluated the test paste using the same measurement criteria.
4. The second group used the same protocol but evaluated the test paste in the first phase and placebo in the second.
5. Measurements were made of the and total volatile sulphur compounds $H_2S$+MeSH. These compounds are implicated in malodour and routinely used for measuring the condition.

The following results were obtained:

Results
TOTAL VSC'S REDUCTION

| Time (days) | 1 | 7 | 14 | 21 | AUC (ng VSC/10 ml) |
|---|---|---|---|---|---|
| Δ% (Placebo-Baseline | 13% | 16% | 19% | 13% | 165.07 |
| Δ% Test product-Baseline | −21% | −4% | −27% | −25% | 123.21 |

AUC = Area under the curve (e.g. total reduction over the 3 week period)
For the overnight measure (Day 1) the test paste significantly reduced the level of total VSC's relative to the placebo ($p < 0.05$).
For the accumulated AUC over the three weeks the test dentifrices significantly reduced the level of VSC's relafive to the placebo ($p < 0.005$).

Example II

The following standard solutions were prepared:

| 0.37 mM $SnF_2$ | (1) |
| 0.033 mM $ZnSo_4.7H_2O$ | (2) |
| 0.37 mM $SnF_2$+0.033 mM $ZnSO_4.H_2O$ | (3) |

Ten replicates of each solution were run in a Bad Breath Indicator Model. This model uses salivary thiol levels as a predictor of oral malodour.

The method exploits the known route for malodour generation in which protein is broken down by bacterial putrefaction into thiol containing compounds, as described by Grigor et al. in J. Dental Research 71, 1348, Abs. 347 (1992); ibid 72, 1347, Abs. 1347 and 1348 (1993). The compounds containing thiol groups are the precursors to the volatile sulphur compounds (hydrogen sulphide and methyl mercaptan). The experimental procedure involves the collection of saliva before, and 30 minutes after, use of the products being evaluated. The saliva samples are then incubated for 24 hours and the thiol concentration measured by the use of a colorimetric indicator (4,4'-bis(dimethylamino)-diphenyl carbinol). A measure of the reduction in the total thiol concentration in saliva is obtained for the test product. The extent of protein degradation that has occurred to generate thiols is taken as a predictor of the ultimate levels of the volatile products hydrogen sulphide and methyl mercaptan and hence the malodour potential of the saliva. The results are shown as the mean Δ A R-SH relative to water controls.

400 μl of each solution was added to the 5 ml saliva samples.

| Solution | Results ΔR-SH |
|---|---|
| (1) | −29.9% |
| (2) | −20.5% |
| (3) | −35.9% |

Statistical Analysis

Analysis was carried out using two sample t-tests.
(a) The level of thiol in saliva with added stannous fluoride (solution (1)) was significantly (p<0.001) different from the level of thiol in water controls.
(b) The level of thiol in saliva with a combination of stannous fluoride and zinc sulphate added (solution (3)) was significantly different (p>0.001) from the level of thiol in saliva with zinc sulphate alone.
(c) The level of thiol in saliva with a combination of stannous fluoride and zinc sulphate added (solution (3) was significantly different (p<0.001) from the level of thiol in saliva with stannous fluoride alone.

The combination of stannous ions and zinc ions was more effective at reducing the levels of thiol in saliva than either stannous or zinc ions alone.

We claim:

1. A method for combating bad breath by reducing the oral cavity level of volatile sulphur compounds including hydrogen sulfide, methyl mercaptan and thiol group precursors of both comprising the steps of:

providing an oral composition comprising from 0.01 to 10% by weight based on the total oral composition of a stannous compound; and applying the stannous compound to volatile sulphur compounds including hydrogen sulfide, methyl mercaptan and thiol group precursors of both considered to be mainly responsible for malodour and bad breath in an oral cavity until the level of thiol in saliva is effectively reduced by said stannous compound.

2. The method according to claim 1 wherein additionally a zinc compound known to effectively reduce oral malodour is present and the reduction of the level of thiol in saliva is more effective than obtained from either stannous ion or zinc ion employed alone.

3. The method according to claim 2 wherein the zinc compound is present in amounts of from 0.05–5% by weight (calculated as zinc ion) of the total oral composition.

4. The method according to claim 2 wherein the stannous and zinc compounds are selected from the group consisting of stannous fluoride, stannous pyrophosphate, zinc citrate trihydrate and mixtures thereof.

5. The method according to claim 1, wherein the stannous compound is at least partially soluble in water or in oral fluids.

* * * * *